(12) United States Patent
Husheer et al.

(10) Patent No.: US 10,631,739 B2
(45) Date of Patent: Apr. 28, 2020

(54) MONITORING VITAL SIGNS (71) Applicant: Cambridge Temperature Concepts Ltd, Cambridge, Cambridgeshire (GB)

(72) Inventors: Shamus Louis Godfrey Husheer, Cambridge (GB); Jonathan Michael Hayes, Cambridge (GB); Oriane Elisabeth Chausiaux, Cambridge (GB)

( * ) Notice: Subject to any disclaimer, the term of this patent is extended or adjusted under 35 U.S.C. 154(b) by 51 days.

(21) Appl. No.: 15/557,198

(22) PCT Filed: Mar. 4, 2016

(86) PCT No.: PCT/GB2016/050591
§ 371 (c)(1),
(2) Date: Sep. 11, 2017

(87) PCT Pub. No.: WO2016/142666
PCT Pub. Date: Sep. 15, 2016

(65) Prior Publication Data
US 2018/0049653 A1 Feb. 22, 2018

(30) Foreign Application Priority Data

Mar. 12, 2015 (GB) .................................. 1504228.6

(51) Int. Cl.
*A61B 5/0205* (2006.01)
*A61B 5/024* (2006.01)
(Continued)

(52) U.S. Cl.
CPC ...... *A61B 5/02055* (2013.01); *A61B 5/02438* (2013.01); *A61B 5/0816* (2013.01);
(Continued)

(58) Field of Classification Search
CPC ......... A61B 5/11; A61B 5/113; A61B 5/1118; A61B 5/02; A61B 5/0205; A61B 5/02055;
(Continued)

(56) References Cited

U.S. PATENT DOCUMENTS

2006/0241511 A1    10/2006  Warmuth
2009/0247849 A1*   10/2009  McCutcheon ..... A61B 5/14551
                                                    600/323
(Continued)

OTHER PUBLICATIONS

Phan D.H. et al., Estimation of respiratory waveform and heat rate using an accelerometer, Engineering in Medicine and Biology Society, pp. 4916-4919, 2008.

*Primary Examiner* — Thaddeus B Cox
(74) *Attorney, Agent, or Firm* — Occhiuti & Rohlicek LLP (57) ABSTRACT

A vital signs monitor for attachment to a human or animal thorax, the monitor having a low power mode and a high accuracy mode and comprising: a motion sensor configured to, in the low power mode, sample movement at a first frequency and, in the high accuracy mode, sample movement at a second frequency, the second frequency being greater than the first frequency; and a processor configured to, in the low power mode, process a series of the one or more movement samples captured by the motion sensor in the low power mode so as to form a measure of activity level, and to, in the high accuracy mode, cause a series of the movement samples captured by the motion sensor in the high accuracy mode to be stored at the vital signs monitor and/or transmitted by means of a transceiver; wherein the processor is configured to prevent the vital signs monitor entering the high accuracy mode from the low power mode when the activity level exceeds a first predefined or dynamic threshold.

14 Claims, 4 Drawing Sheets

(51) Int. Cl.
  *A61B 5/11* (2006.01)
  *A61B 5/113* (2006.01)
  *A61B 5/08* (2006.01)
  *A61B 5/00* (2006.01)
(52) U.S. Cl.
  CPC ........... *A61B 5/1118* (2013.01); *A61B 5/1135* (2013.01); *A61B 5/6823* (2013.01); *A61B 5/7278* (2013.01); *A61B 5/113* (2013.01); *A61B 2560/0209* (2013.01); *A61B 2562/0219* (2013.01)
(58) Field of Classification Search
  CPC ... A61B 5/024; A61B 5/02438; A61B 5/0245; A61B 5/6823; A61B 5/7278
  See application file for complete search history.

(56) References Cited

U.S. PATENT DOCUMENTS

| | | |
|---|---|---|
| 2011/0021928 A1 | 1/2011 | Giovangrandi et al. |
| 2011/0066041 A1 | 3/2011 | Pandia et al. |
| 2012/0029314 A1 | 2/2012 | Paquet et al. |
| 2012/0083705 A1* | 4/2012 | Yuen ................. A61B 5/0002 600/508 |
| 2013/0072765 A1* | 3/2013 | Kahn .................. A61B 5/01 600/301 |
| 2013/0137946 A1* | 5/2013 | Geske ............... A61B 5/02433 600/324 |
| 2014/0135593 A1* | 5/2014 | Jayalth ............... A61B 5/0022 600/301 |
| 2014/0135612 A1 | 5/2014 | Yuen et al. |
| 2014/0215246 A1* | 7/2014 | Lee ..................... G06F 1/3206 713/323 |
| 2014/0275854 A1 | 9/2014 | Venkatraman et al. |
| 2014/0358472 A1 | 12/2014 | Goel et al. |
| 2015/0057967 A1* | 2/2015 | Albinali ............... A61B 5/1118 702/150 |
| 2015/0094544 A1* | 4/2015 | Spolin ................ A61B 5/7275 600/301 |
| 2015/0374310 A1* | 12/2015 | Lee .................... A61B 5/7285 600/483 |
| 2016/0354014 A1* | 12/2016 | Lobner ............... A61B 5/0004 |

* cited by examiner

MONITORING VITAL SIGNS

CROSS-REFERENCE TO RELATED APPLICATIONS

The application claims the benefit of, and priority to, International Application No. PCT/GB2016/050591, entitled "Monitoring Vital Signs," and filed Mar. 4, 2016, which claims the benefit of, and priority to, UK application No. GB 1504228.6, filed Mar. 12, 2015.

BACKGROUND OF THE INVENTION

This invention relates to monitoring vital signs in humans and animals, in particular one or more of heart rate, respiration rate and temperature.

Conventionally, heart or pulse rates are determined through measurements of the electrical activity of the heart. For example, an electrocardiograph (ECG) uses two or more electrodes attached about the chest to measure the electrical activity of the heart and hence determine heart rate. In a hospital environment, electrocardiographs offer an accurate measurement of heart rate as well as detailed information about the activity of the heart muscles. More basic monitors of heart rate activity are available, such as the type of heart rate monitor worn by athletes which typically determine heart rate but do not provide further information of the type which can be useful to diagnose heart problems. Heart rate monitors for sports typically include a chest strap comprising the electrodes for measuring the electrical activity of the heart and a device to which the measurements are transmitted for processing into a heart rate value, for example a watch or smartphone. Such chest straps can be uncomfortable to wear and for reliable operation require the user to sweat or prepare the electrodes of the chest strap with a conductive gel to electrically couple the electrodes to the skin.

Respiration rate can be measured in various ways, although it is often not directly measured in a clinical setting (measurements of oxygen saturation in the blood is typically of more immediate value). Various kinds of pneumographic apparatus is available for directly measuring the rate of respiration which have different principles of operation. This includes apparatus which measures the expansion and contraction of the chest through the use of a flexible strap attached about the chest, and apparatus which measures the changes in electrical resistance across the chest cavity as the user's lungs expand and contract. Other types of apparatus directly measure the inhalation and exhalation of air through a patient's mouth or breathing tube.

Pneumographic apparatus is generally bulky and designed for use in a hospital or sports science environment.

Various applications are available for smartphones which utilise the accelerometer present in smartphones to determine the respiratory rate of a user when the smartphone is placed on the chest of a user lying in a supine position. It has also been established by Kwon et al. in Validation of heart rate extraction through an iPhone accelerometer, Conference Proceedings of the IEEE Engineering in Medicine and Biology Society 2011; pp. 5260-5263, that the accelerometer of an iPhone can be used to capture an estimate of heart rate by strapping the phone to the chest. It is however uncomfortable to wear a smartphone in this manner for long periods of time and the power demands of operating a smartphone in this manner do not allow its battery to support such an operation for more than a few hours. Smartphone applications are also available which capture a rough estimate of heart rate at a moment in time using the smartphone's camera.

Neither the conventional apparatus used in hospitals to measure heart and respiration rate, nor the apps available on smartphones, allow the vital signs of a user to be monitored for extended periods of time as they go about their daily activities.

BRIEF SUMMARY OF THE INVENTION

According to a first aspect of the present invention there is provided a vital signs monitor for attachment to a human or animal thorax, the monitor having a low power mode and a high accuracy mode and comprising:

a motion sensor configured to, in the low power mode, sample movement at a first frequency and, in the high accuracy mode, sample movement at a second frequency, the second frequency being greater than the first frequency; and a processor configured to, in the low power mode, process a series of the one or more movement samples captured by the motion sensor in the low power mode so as to form a measure of activity level, and to, in the high accuracy mode, cause a series of the movement samples captured by the motion sensor in the high accuracy mode to be stored at the vital signs monitor and/or transmitted by means of a transceiver; wherein the processor is configured to prevent the vital signs monitor entering the high accuracy mode from the low power mode when the activity level exceeds a first predefined or dynamic threshold.

The processor may be further configured to, in the high accuracy mode, process the series of movement samples so as to form an estimate of at least one of heart rate and breathing rate.

The processor may be further configured to, in the high accuracy mode, process the series of movement samples in dependence on the estimated heart rate and/or breathing rate so as to form an estimate of the amplitude of movements of the vital signs monitor due to heartbeat and/or breathing.

The vital signs monitor may be configured to attempt to enter high accuracy mode according to a predefined schedule or in response to a command received at a transceiver of the vital signs monitor.

In use, the vital signs monitor may be coupled to a data processing system by means of the transceiver and the command is generated at the data processing system in response to an indication as to the health or perceived wellbeing of the wearer of the vital signs monitor.

The vital signs monitor may further comprise a temperature sensor arranged to, in the low power mode and in use, capture a temperature of the wearer of the vital signs monitor.

The vital signs monitor may be configured to attempt to enter high accuracy mode and/or to increase the frequency of attempts according to the predefined schedule in response to the temperature of the wearer and/or the variance of the temperature being below a predefined or dynamic threshold in the low power mode for a first predefined or dynamically-determined period of time.

The vital signs monitor may be configured to attempt to enter high accuracy mode in response to the activity level of the user being below a second predefined or dynamic threshold for a second predefined or dynamically-determined period of time.

The vital signs monitor may be configured to attempt to enter high accuracy mode a predetermined length of time following the processor preventing the vital signs monitor from entering the high accuracy mode.

The vital signs monitor may be configured to revert to the low power mode once the motion sensor has stored and/or transmitted the movement samples.

The processor may be configured to form the measure of activity level in dependence on the orientation of the vital signs monitor as indicated by the one or more movement samples.

The measure of activity level may represent a change in orientation over the one or more movement samples.

The motion sensor may be an accelerometer.

The second frequency may be at least twice the highest expected breathing rate appropriate to the intended human or animal subject.

The first frequency may be at least an order of magnitude lower than the second frequency.

According to a second aspect of the present invention there is provided a method for measuring heart rate at a data processing system comprising a vital signs monitor for attachment to a human or animal thorax, the method comprising:
  at the vital signs monitor, sampling movement at a first frequency;
  processing the movement samples so as to form an estimate of respiratory rate;
  using the estimated respiratory rate to form a coarse estimate of heart rate;
  selecting a second frequency according to the coarse estimate of heart rate;
  at the vital signs monitor, sampling movement at the second frequency; and
  processing the movement samples acquired at the second frequency so as to form a fine estimate of heart rate.

Forming the coarse estimate of heart rate may comprise multiplying the estimated respiratory rate by a factor of approximately 8 to 12.

The data processing system may comprise a data processor wirelessly coupled to the vital signs monitor, the data processor being configured to receive the movement samples acquired at the second frequency from the vital signs monitor and to perform said processing of the samples so as to form the fine estimate of heart rate.

The processing of the movement samples so as to form an estimate of respiratory rate may be performed at the data processor.

The data processor may be a smartphone.

The method may further comprise forming a fine estimate of respiratory rate from samples acquired at the second frequency.

The processing of the movement samples so as to form a fine estimate of heart rate may comprise:
  decomposing the movement samples into component frequencies;
  based on the estimated heart rate, searching for a peak frequency within a range of possible frequencies representative of heart rate;
  selecting the peak frequency as the fine estimate of heart rate.

BRIEF DESCRIPTION OF THE DRAWINGS

The present invention will now be described by way of example with reference to the accompanying drawings. In the drawings.

DETAILED DESCRIPTION OF THE INVENTION

The following description is presented by way of example to enable any person skilled in the art to make and use the invention. The present invention is not limited to the embodiments described herein and various modifications to the disclosed embodiments will be readily apparent to those skilled in the art.

Figure 1:
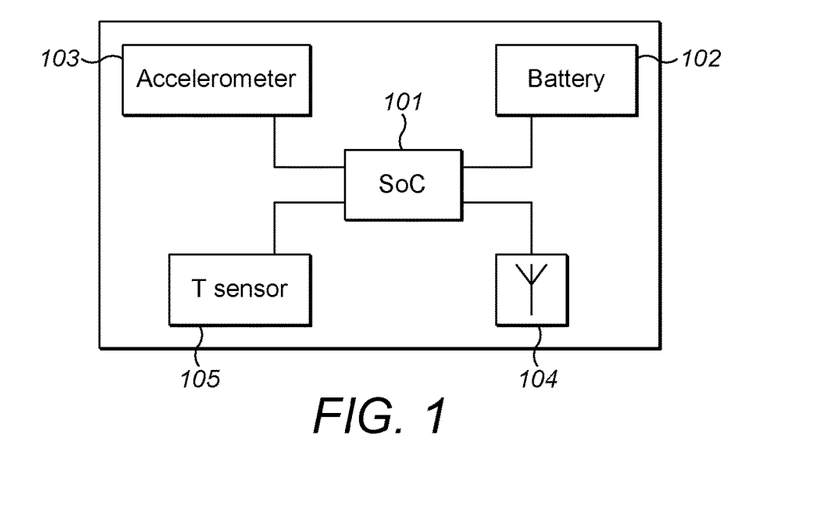
FIG. 1 is a schematic diagram of a wearable vital signs monitor.

FIG. 1 is a schematic diagram of a wearable vital signs monitor adapted for measuring one or more vital signs of a wearer of the sensor. The vital signs monitor 100 includes a processor 101 (e.g. a low power system-on-chip or SoC), a battery 102, a motion sensor 103, and a wireless transceiver 104. In the example shown in FIG. 1, the motion sensor is an accelerometer and therefore measures acceleration. It is preferred that the motion sensor measures acceleration or a higher derivative of velocity because these types of motion provide good sensitivity to movements of the chest due to heartbeat and breathing. More generally, it could be any suitable device (e.g. a gyroscope) for measuring the movement of the vital signs monitor 100 due to the movement of the chest with breathing and/or heartbeat. Vital signs monitor 100 may optionally further include receiving unit 105 for receiving information relating to the wearer. In the example shown in FIG. 1, the receiving unit is a temperature sensor arranged to capture temperature data indicative of a temperature of the wearer. In other examples, the receiving unit could receive any other information relating to the wearer, including, for example, physiological information (e.g. through measurement or inferred from received data), information about the activity or environment of the wearer, or indications from the user as to their perceived state of health.

Wearable vital signs monitor 100 may be adapted for measuring one or more of respiration rate and heart rate. The vital signs monitor is preferably adapted for attachment to the thorax of a subject human or animal body such that the monitor is subject to the movements of the thorax as a result of respiration and/or heartbeat. For example: if vital signs monitor 100 is configured to measure respiration rate, the monitor may be adapted to be worn about the chest (thorax) such that the movement of the chest due to the inhalation and exhalation of air results in a corresponding movement of the monitor, and if vital signs monitor 100 is configured to measure heart rate, the monitor may be adapted to be worn about the chest (thorax) such that the movement of the chest due to the beating of the heart results in a corresponding movement of the monitor.

The vital signs monitor 100 is preferably adapted for wear at the chest (thorax) at a location where that it can detect movement due to both breathing and the beating of the heart. It has been found that a particularly advantageous position for locating the monitor in order to allow both respiration and heart rates to be measured is on the lateral part of the thorax closest to the heart (on the left side in most people). The monitor may be located in or close to the arm pit.

The wearable vital signs monitor may be held against the body in any suitable manner, including by adhesive for attachment directly to the skin, held within an elasticated strap, or within clothing (e.g. in a pouch in a bra or elasticated vest). It is important that the monitor is mechanically coupled to the body such that movements of the body result in corresponding movements of the monitor.

Figure 2:
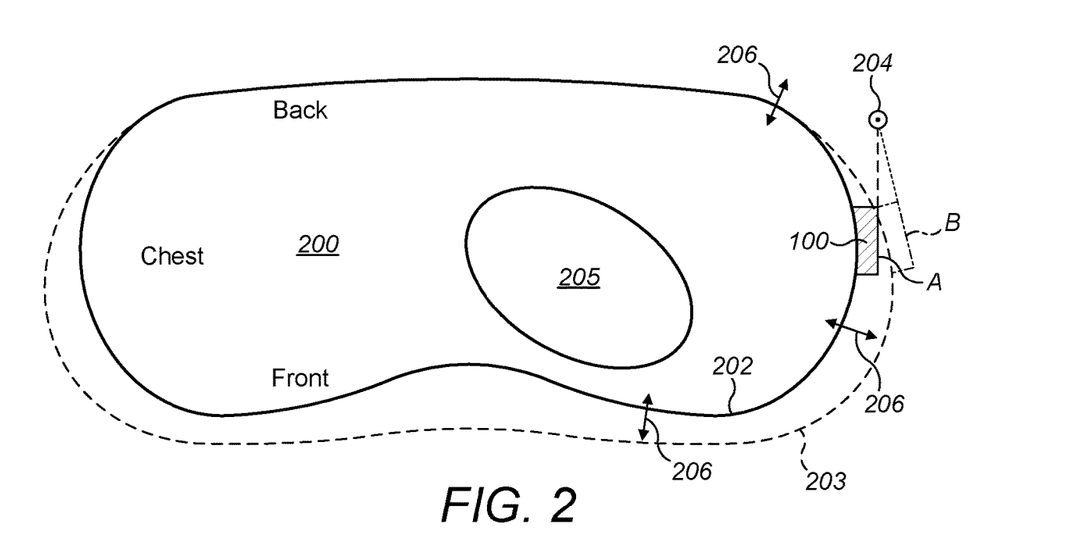
FIG. 2 shows the vital signs monitor in-situ on a human chest.

FIG. 2 shows a cross-section of a human chest 200 to which vital signs monitor 100 has been attached to the skin at an advantageous location by means of adhesive. The monitor is located on the left lateral side of the chest just below the armpit. The figure illustrates the movement 201 of the chest wall 202 as the person inhales: as the lungs inflate, the chest wall 202 moves to position 203. Consequently, the vital signs monitor 100 moves about an axis 204 from position A to position B. This movement can be detected by the accelerometer 103 of the monitor.

FIG. 2 also illustrates the movement of the chest wall due to the beating of the heart. The heart is roughly located at position 205. As the heart beats it causes the chest wall 202 to move in and out by a small amount, as indicated by arrows 206. This movement can be detected by the accelerometer 103 of the monitor.

It will be appreciated from FIG. 2 that the movements of the chest wall associated with breathing and the beating of the heart can be detected by a vital signs monitor located at a range of positions on the chest wall. Locating the monitor on the lateral side of the chest wall has the advantage that the accelerometer 103 can be configured to look for movements about axis 206 (e.g. a change in tilt of the sensor). This helps the accelerometer to distinguish the movement of the chest wall due to breathing from other gross movements of the chest, such as those due to the person moving around (e.g. walking, driving, and performing other daily activities).

The inventors have appreciated that it is important that the mass of the wearable monitor is as low as possible since this enables high sensitivity to be achieved and/or a cheaper accelerometer. In practice, this means minimising the size of the battery which will typically be the dominant factor in the mass of a wireless wearable device. The battery could be a kinetic energy recovery device which generates power from the movement of the wearer. Embodiments are also envisaged in which the monitor comprises two parts: a first part which includes the motion sensor, and a second part which includes a battery to power the motion sensor. Lightweight, flexible wires could be used to couple the motion sensor to the battery.

Whilst accelerometers are available with sufficient precision to measure the movements of a chest wall due to respiration and heartbeat, such accelerometers typically draw a significant amount of power. In order to achieve a reasonable battery life for a wearable vital signs monitor which operates wirelessly, a large battery could be provided. However, increasing the size of the battery would increase the mass of the monitor which decreases the sensitivity of the vital signs monitor. This can be appreciated from Newton's second law $F=ma$: increasing the mass of the monitor decreases its acceleration for a given force applied to the monitor by the movement of the chest wall. For example, a 150 gram smartphone provided with an accelerometer having a sensitivity of $1/1000$ g (where g is the acceleration due to gravity at the earth's surface) is able to detect the movement of a person's chest so as to allow their rate of respiration to be determined. Using a sensor with a mass of 7 grams enables the same movement to be detected with an accelerometer having a sensitivity of only $1/50$ g—a 20-fold reduction or about 4 bits of precision. Thus a lighter vital signs monitor allows either greater sensitivity for a given model of accelerometer, or a cheaper, less precise accelerometer to be used for the same sensitivity to movement. A ST Microelectronics LIS3DLH accelerometer has been found to offer a good balance between sensitivity and cost.

It is not straightforward to achieve the sensitivity required to detect heart and respiration rates in a wearable vital signs monitor having a battery life of more than several hours. It is typically desired that wearable devices for monitoring physiological parameters have a battery life of at least several days and preferably several weeks. Unlike the use of heart rate monitors to measure heart rate during intense physical activity, it is generally desired that devices for monitoring physiological parameters can operate as long as possible while regularly measuring those parameters. This is because the device cannot monitor the wearer when it is being recharged or having its battery replaced (which may lead to key data not being captured) and the less the user must do to maintain the device the greater the convenience for the user.

The monitor may be packaged in such a way that the battery cannot be accessed—for example, the monitor may be sealed in one or more materials (e.g. a plastic or resin) which protect the electronics of the monitor from liquids and damage. The monitor may be disposable.

The operation of vital signs monitor 100 worn at or around the location shown in FIG. 2 will now be described by way of example. As has been described, this location allows the monitor to measure both heart and respiration rates.

In order to start measuring one or more vital signs of the wearer, the processor of the vital signs monitor may be configured to receive a trigger. A trigger could be, for example, an appropriate request received by transceiver 104, a trigger from a timer running at monitor 100 (e.g. the monitor could be configured to periodically perform heart rate measurements), or a condition being satisfied at the processor 101 (e.g. activity measurements by the vital signs monitor indicating that the movement activity of the wearer is below some threshold).

A trigger may be generated in dependence on other data captured by the monitor or provided by the wearer (e.g. to a smartphone coupled arranged to transmit a trigger to the monitor). For example, in the case that receiving unit 105 is a temperature sensor, the monitor or another device which is configured to periodically or continuously receive temperature data from the monitor may generate a trigger to cause the monitor to measure respiration and or heart rate. It can be advantageous to trigger vital signs measurement when the measured temperature (or a temperature value derived from the measured temperature) is below some predefined or dynamic threshold and/or the temperature data indicates that the temperature of the wearer is stable (e.g. a measure of the variation in temperature is below some predefined or dynamic threshold). Similarly, it can be advantageous to trigger vital signs measurement when the activity level is below some predefined or dynamic threshold—the activity level can be indicated by the wearer (e.g. by means of appropriate data entry into a smartphone coupled to the monitor) or captured by the motion sensor in a low power mode of the monitor (e.g. as described below).

Vital signs measurement may be triggered by other data provided by the user (e.g. by means of appropriate data entry into a smartphone coupled to the monitor). Such other data may include an indication of how the user is feeling. For example, the rate at which the monitor performs capture of heart rate and/or respiration data may be selected in dependence on how the user is feeling: if the user indicates (e.g. through a smartphone app) that they feel unwell, the monitor may be configured to trigger more frequently for some length of time (e.g. that day or the next 24 hours), and/or the monitor may be immediately triggered to capture vital signs data.

It can be advantageous to trigger vital signs measurements in dependence on an assessment of the health of the wearer (e.g. by an app running at a smartphone coupled to the monitor). For example, if a temperature sensor 105 indicates that the user is running a high temperature whilst the activity level of the wearer is determined to be low, one or more vital signs measurements may be initiated and/or the rate at which the monitor is triggered to capture vital signs data may be increased for some length of time (e.g. that day or the next 24 hours).

It can also be advantageous to trigger vital signs measurement when the temperature and/or activity data indicates that the wearer is at rest (e.g. asleep). This enables the capture of vital signs during rest/sleep periods when heart rate and respiration rate can be most easily captured from acceleration data (and hence at minimal power), and can be useful for monitoring certain medical conditions.

In the present example, the vital signs monitor 100 adopts a two-step approach to capturing respiration and heart rates. Recognising that the rate of respiration is almost always going to be less than heart rate and with a view to minimising energy usage, the monitor determines respiration rate from measurements of movement performed at a first, lower sampling rate, and determines heart rate from measurements of movement performed at a second, higher sampling rate. Furthermore, the monitor uses the respiration rate to form an initial estimate of heart rate which enables the monitor to select an energy-efficient sampling rate for capturing movement data to be used in the determination of heart rate.

An exemplary method performed by the vital signs monitor follows below.

1. Processor 101 receives a trigger to start measuring respiration rate.
2. The processor causes the accelerometer to take a first set of coarse movement measurements at some initial frequency for several seconds—in order to achieve sufficient accuracy, preferably at least 5 breaths, which is typically at least 30 seconds. The initial frequency may be a default frequency (around 2 Hz has been found to work well) or may be formed in dependence on previous measurements of heart or breathing rates. The initial frequency may be selected in dependence on the measured activity level—for example, if the activity level is high in some period prior to receiving the trigger to starting measuring respiration rate, a higher initial frequency may be used than if the activity level is low on the basis that the wearer is moving about and may therefore have a higher heart rate. The rate of respiration can generally be determined from this captured movement data (for example, see FIG. 3 and the related description below). If the monitor cannot identify the respiratory rate from the data, the monitor may be configured to increase the sampling frequency so as to capture a second set of coarse measurements from which to repeat the determination of the respiratory rate—this could be necessary in cases where the respiratory rate is very high.
3. Once the rate of respiration has been identified, the monitor roughly estimates the likely heart rate based on a guess that the heart rate is typically around 10 times greater than the respiration rate (i.e. as the rate of breathing increases, the heart rate also increases). For example, a breathing rate of 10 breaths per minute suggests an estimated heart rate of 100 bpm (beats per minute). This observation can be used to identify a sampling rate that is high enough to allow the accelerometer to capture heart rate but which is not too high so as to avoid unnecessary energy use. It has been found that around 10 samples are required per heartbeat in order to reliably detect the heart rate: so in the present example, based on the estimated heart rate a sampling frequency of at least 17 Hz would be used. Good performance is possible with a sampling rate which equates to at least 5 samples per heartbeat on the basis of the estimated heart rate, preferably at least 8 samples per heartbeat on the basis of the estimated heart rate, and most preferably at least 10 samples per heartbeat on the basis of the estimated heart rate. It is however also preferred that the sampling rate does not exceed 15 samples per heartbeat (more preferably 12 samples per heartbeat, and most preferably 10 samples per heartbeat) on the basis of the estimated heart rate so as to avoid excessive energy use.
4. The monitor may store the coarse data or transmit it to another entity for storage or processing by means of transceiver 104.
5. The processor causes the accelerometer to take a set of fine measurements around (and, recalling that the estimated heart rate is only a rough estimate which may be low, preferably slightly above) the identified sampling frequency. For example, in the given example, the accelerometer may be configured to capture acceleration data at around 20 Hz for long enough to capture at least several heartbeats (preferably at least 20, or around 15 seconds) and enable the heart rate of the wearer to be identified.
6. The accelerometer may be optionally further configured to re-determine the respiration rate from the higher-resolution fine accelerometer data captured at the higher sampling rate. This can potentially improve the estimate of the respiration rate.
7. The monitor may store the fine data or transmit it to another entity for storage or processing by means of transceiver 104.

Operating the accelerometer at a sampling frequency which is sufficient to capture even very high possible heart rates consumes a substantial amount of energy. Using this two-step approach minimises energy usage since it avoids operating the accelerometer at a sampling frequency which is higher than required to accurately capture the likely heart rate of the wearer.

Processor 101 may determine respiration and heart rates according to any suitable algorithm. For example, an FFT (Fast Fourier Transform) may be performed on the captured movement data so as to decompose the samples into their component frequencies. The respiration rate can be identified from a frequency peak within the range of possible respiration rates (10-60 breaths per minute but more typically 12-20 breaths per minute); similarly, heart rate can be identified from a frequency peak within the range of possible heart rates (30-220 beats per minute but more typically 60-120 beats per minute). Typically the respiration/heart rate will be the dominant rate within the possible range of values. More accurate ranges for the possible respiration and heart rates may be identified from information about the wearer: for example, their age, physical condition and any medical problems suffered from. Such information could be provided to the entity analysing the captured data for respiration/heart rate (e.g. the vital signs monitor or another processing entity to which the captured data is sent) so as to narrow the frequency ranges within which the peaks are to be identified. The above two-step approach provides a reliable mechanism for correctly identifying whether a frequency peak relates to respiration or heartbeat: by first identifying the respiration rate, a guess at the heart rate can be made and verified from the data. For this reason it can be advantageous to form final estimates for respiration and heart rates from an FFT of fine movement data captured by the motion sensor.

Figure 5:
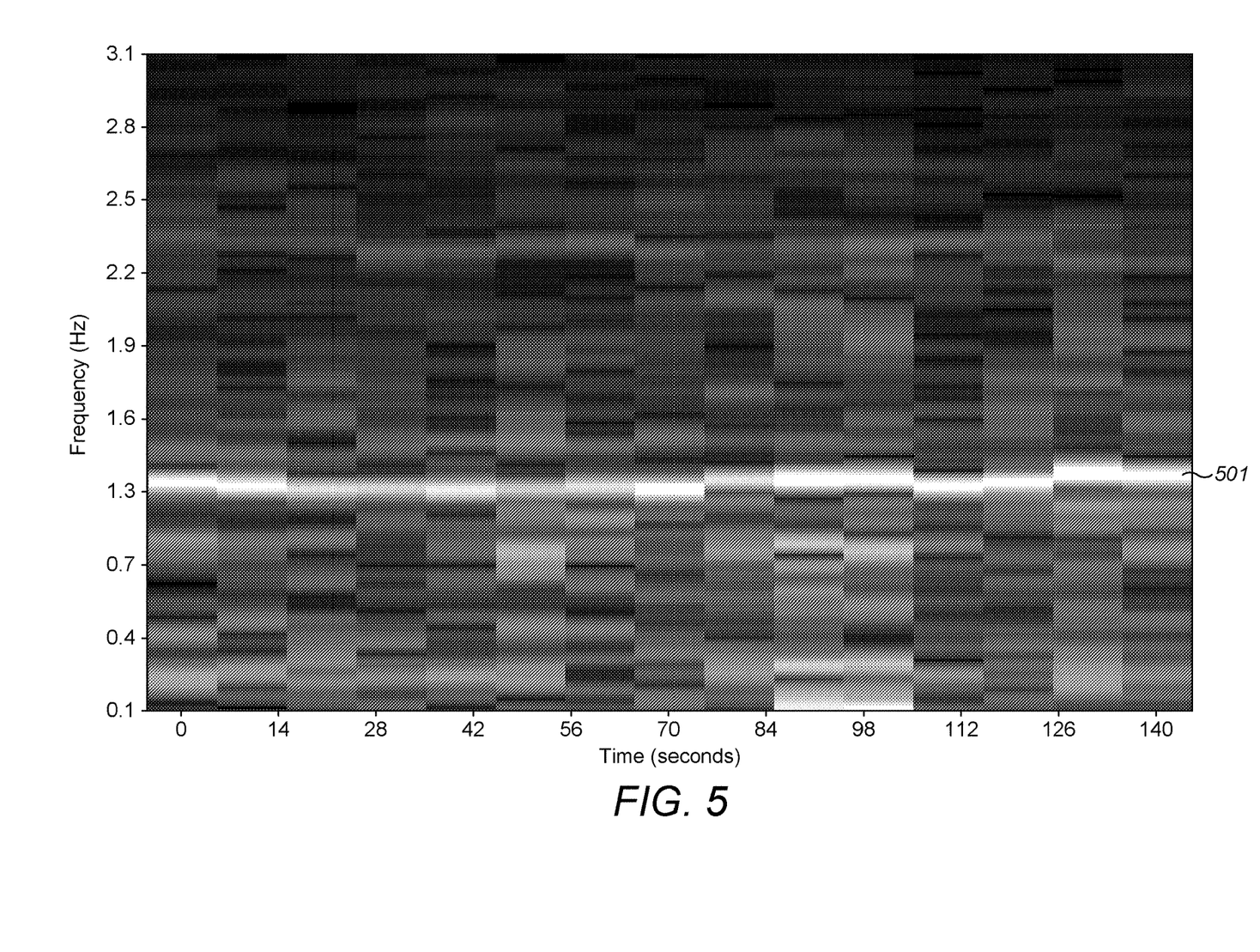
FIG. 5 shows a spectrogram of sampled movement data captured by a vital signs monitor.

FIG. 5 shows a spectrogram of sampled movement data captured by a vital signs monitor attached to the chest in the manner shown in FIG. 2. In the figure, the strength of frequencies are indicated on a scale from black to white, with low strengths being indicated by dark shades and high strengths by light shades. It can be observed that a peak 501 is visible at a frequency of approximately 1.15 Hz, which in this example corresponds to a heartbeat of 69 beats per minute.

Typically an accelerometer will provide movement information for more than one axis. It is generally advantageous to use the accelerometer measurements for the axis whose values are most rapidly varying and/or which exhibit the greatest variation. For example, the vital signs monitor could select as the coarse or fine measurements the values from the accelerometer axis having the greatest variance—such a determination could be performed periodically or each time measurements are captured. Alternatively, measurements from more than one accelerometer axis could be combined to form a series of movement samples as the output from the accelerometer—e.g. values from a pair of accelerometer axes could be summed in some way (say, a simple sum or a sum of squares) or preferably principle components analysis could be performed so as to find the direction of greatest variation of acceleration and form an output sample representing the magnitude of the acceleration in that direction. Similar arrangements may be possible for other types of motion sensor. The accelerometer could be oriented in the vital signs monitor such that when the monitor is attached to the wearer in the intended manner, one or more axes of the accelerometer are appropriately oriented to detect movement due to respiration and/or breathing. In some cases, it may be advantageous to determine respiration and heart rates from movement data captured on different accelerometer axes.

The vital signs monitor may itself process the captured movement data at processor 101 in order to form an estimate of heart and/or respiration rates. Alternatively the monitor may store the movement data at the monitor (e.g. at a memory of SoC 101) and/or transmit the movement data to a more powerful data processing device (e.g. a smartphone or cloud server) for processing so as to form an estimate of heart and/or respiration rates. This minimises the power consumption of the monitor and, when performed at higher power data processing systems, enables more sophisticated algorithms to be used.

It is advantageous to apply signalling to the raw movement data captured by the motion sensor prior to analysing the data to determine the respiration and breathing rates. For example, movement data from one or more axes of an accelerometer may be passed through a first filter so as to generate a breathing signal, and through a second filter so as to generate a heartbeat signal.

Figure 3:
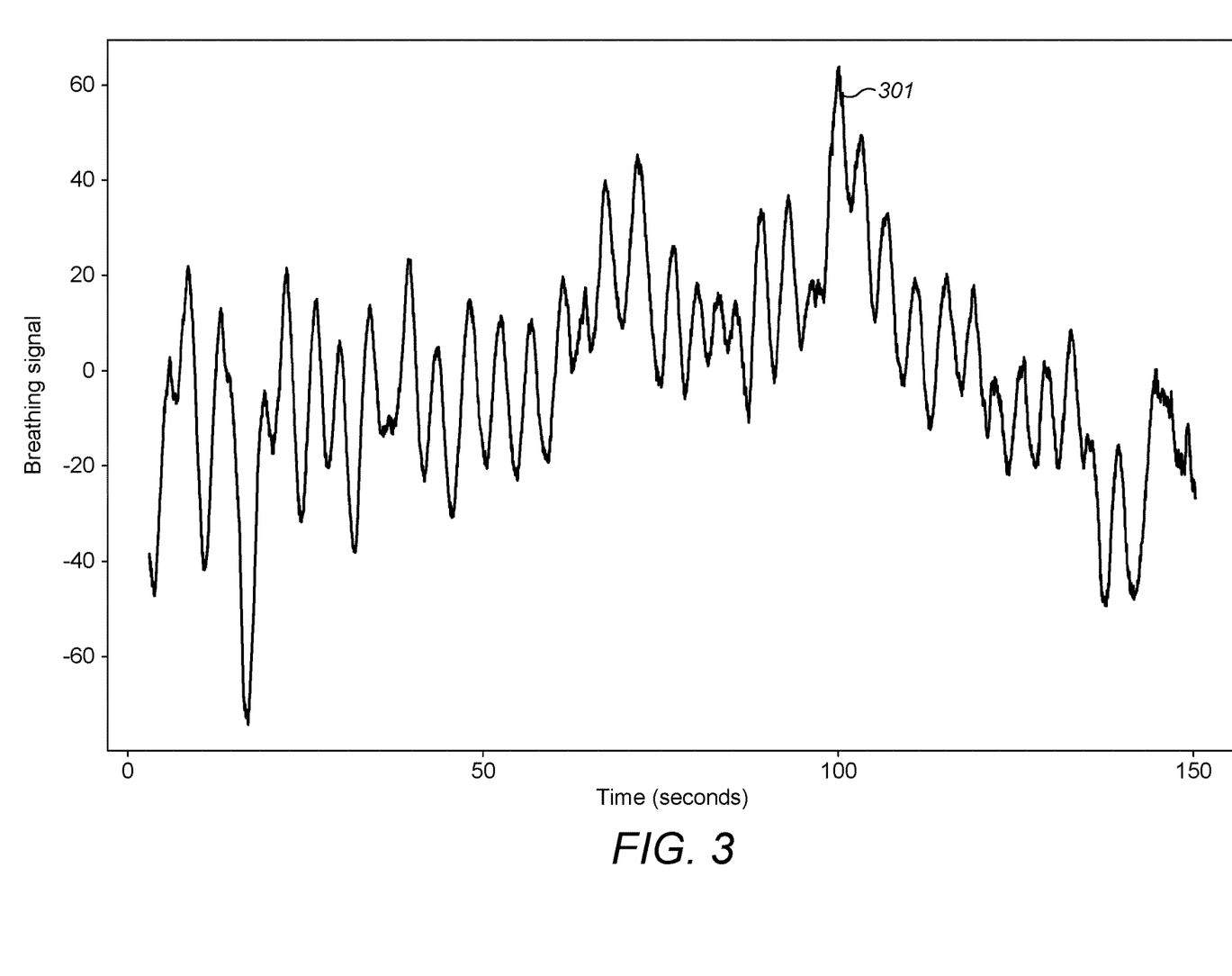
FIG. 3 shows An example of a breathing signal captured by a vital signs monitor attached to the chest.

An example of a breathing signal captured by a vital signs monitor attached to the chest is shown in FIG. 3. The breathing signal is a dimensionless measure of the acceleration measured at the accelerometer from fine data captured by the monitor and filtered so as to remove features due to heartbeat (e.g. by applying a low pass filter with a cut-off frequency of a few times—e.g. 2 times—the expected breathing rate determined by the monitor). In FIG. 3, the strong periodic variation in the breathing signal 301 represents the rate of respiration, which is imposed upon a moving baseline due to the wearer's movements.

Figure 4:
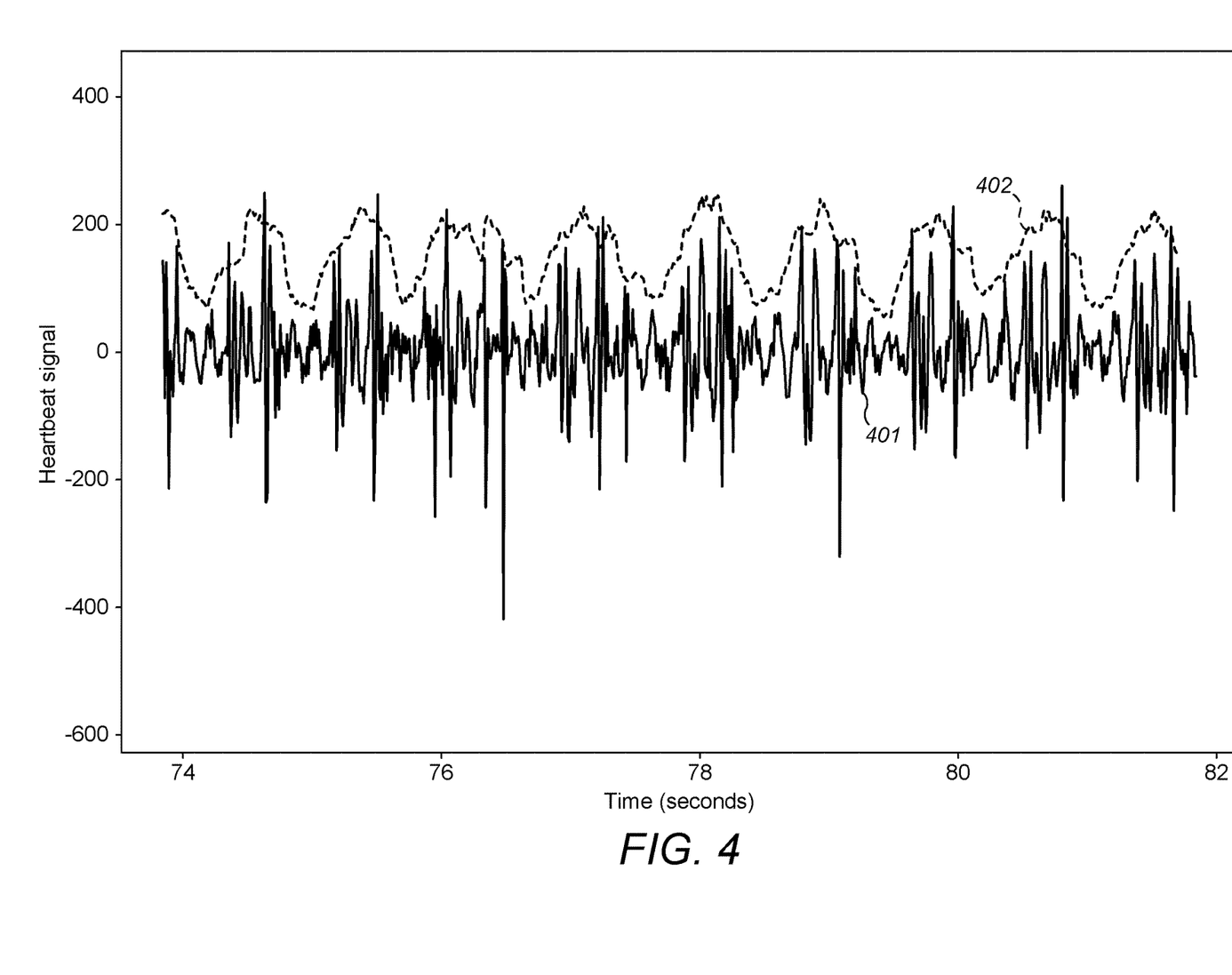
FIG. 4 shows an example of a heartbeat signal captured by a vital signs monitor attached to the chest.

An example of a heartbeat signal captured by a vital signs monitor attached to the chest is shown in FIG. 4. The heartbeat signal is a dimensionless measure of the acceleration measured at the accelerometer from fine data captured by the monitor and filtered so as to remove features due to breathing (e.g. by applying a high pass filter with a cut-off frequency of a few times—e.g. 2 times—the expected breathing rate determined by the monitor). In FIG. 4, the heart rate can be identified from a periodic change in the amplitude of the heartbeat signal 401, as indicated by curve 402.

Further data relating to nature of the breathing and/or heart rate measured by the monitor may be captured from the amplitude of the motion (in this present example, acceleration) due to the breathing and/or heart rate. For example, once the monitor has identified the frequency of breathing (the respiration rate), the monitor can measure the amplitude of the variations at that frequency in the captured movement data. The measured amplitude would typically be a dimensionless value, such as the breathing signal shown in FIG. 3. However, by comparison to stored values representing large and small amplitudes in breathing and/or heart rate, the vital signs monitor may determine whether the measured amplitude is indicative of shallow or deep breathing for the wearer. Such stored values could be determined empirically for the wearer: e.g. through the wearer or a medical professional indicating to the monitor (perhaps by entering data into a smartphone coupled to the monitor) when the wearer's breathing is shallow or deep. This approach can calibrate to a particular wearer the data provided by the monitor as to the amplitude of breathing and/or heart rate, allowing conclusions to be drawn as to the depth of respiration/strength of heart rate relevant to the wearer.

The combination of breathing rate and amplitude data can be useful in diagnosing the onset of particular conditions: for example, such a combination can help identify changes in breathing indicative of an asthma attack or difficulty breathing due to COPD (both indicated by fast, shallow breathing). Furthermore, because fast breathing is normally correlated with shallow breaths and slow breathing is normally correlated with deep breaths, the vital signs monitor may perform a check that the determined breathing rate is correct. For example, the monitor could be configured to calculate an estimate of the expected range of amplitudes of the respiration/heart rate based on a measured respiration/heart rate and to check that the measured amplitude of the breathing/heart rate signal lies within the estimated range. If the amplitude lies outside the range, the monitor may discard the measured breathing/heart rate and, for example, re-perform the measurement of breathing/heart rate or wait until the next trigger.

Such estimates of amplitude of movement due to heartbeat and/or breathing may be performed at the vital signs monitor (e.g. at a processor) or at a data processing system coupled to the monitor and configured to receive movement data from the monitor.

It can be advantageous to use the accelerations measured by a smartphone or other personal electronic device comprising an accelerometer to filter out movements of the user from signals representing the movements of the monitor due to breathing and heartbeat. This is on the basis that a personal electronic device is likely to be subject to the same gross movements of the user as the vital signs monitor worn by the user. Such filtering could be performed at the monitor in dependence on movement information received at receiving unit 105, or preferably at a data processing device arranged to receive movement data from both the smartphone or other personal device and the vital signs monitor. The data processing device could be the smartphone. For example, the smartphone could be configured to periodically receive a transmission from a vital signs monitor which is configured to capture movement data according to some predefined schedule for determination of respiration and/or heart rates. Provided the clocks of the smartphone and vital signs monitor were synchronised, the smartphone could be configured to record the output of its accelerometer according to the same schedule such that movement data for the smartphone is available for the same periods as movement data captured by the vital signs monitor. The smartphone could be configured to determine which of its axes most closely correlate to the movement data captured by the vital signs monitor and, following suitable scaling, subtract the output of that axis of the smartphone's accelerometer from the movement data captured by the vital signs monitor so as to yield a signal from which gross movements of the wearer have been filtered.

Rather than continuously measuring breathing and heart rate, monitor 100 may be configured to measure vital signs only from time to time: for example, this may be periodically, in response to a request received at the monitor, or in response to other data received at the monitor (e.g. at receiving unit 105). With a low power accelerometer (e.g. an ST Microelectronics LIS3DSH) and a battery (e.g. a CR2012) selected such that the monitor weighs less than 10 g, this allows the monitor to achieve a battery life of several weeks. The monitor may be arranged to monitor the vital signs of a human or animal whose life is not in immediate danger (i.e. does not require truly continuous monitoring in a hospital) as they go about their daily activities.

Preferably the vital signs monitor is configured to capture movement data from its motion sensor according to a predefined schedule. It has been found that a schedule of, for example, between once every few minutes to hourly offers good resolution as to the vital signs of the wearer whilst enabling a battery life of several weeks in a package light enough to be worn without discomfort to the wearer.

It is advantageous if the vital signs monitor is configured to avoid capturing movement data in order to detect heart rate and/or the rate of respiration when the activity of the wearer is high. This avoids the monitor wasting energy attempting to detect vital signs when the wearer is engaging in strenuous activity (e.g. running, although walking may also be avoided). It has been found that the rate of respiration (breathing) is often synchronised with the rhythm of footsteps which can make it substantially more difficult for the monitor to detect respiration (e.g. the acceleration of the monitor due to movement of the chest wall can be masked by larger accelerations of the monitor due to the footfalls of the wearer). The relatively weak impulses experienced by the monitor due to the beating of the heart can also be dominated by its accelerations (vibrational and/or due to gross movement) when the activity of the wearer is high.

A vital signs monitor configured to avoid capturing movement data for the detection of heart rate and/or the rate of respiration when the activity of the wearer is high will now be described, again with reference to FIG. 1. Any of the features described below may be combined with those of a vital signs monitor as described in any of the examples given above.

It is advantageous if the vital signs monitor is operated in two modes. In a first, low power mode, the motion sensor is configured to periodically measure its movement at a low sampling rate, for example, of the order of 30 seconds to a few minutes (a period of 30 seconds has been found to work well). A very short measurement of movement can be captured each time the motion sensor measures movement. The motion sensor may be configured to periodically capture measurements in any suitable manner, including: in response to a polling signal from the processor, and based on a timer running at the motion sensor. Between measurements, the motion sensor would preferably be in a low power state/substantially powered down. The movement measurements performed in low power mode are used to form a measure of the activity level of the wearer. Some accelerometers offer a low power mode in which movement data can be captured at a low sampling rate; other accelerometers may be polled at a low rate in order to capture data at a low temporal resolution.

Any suitable measure of activity level could be used. For example, one or more samples may be captured (preferably no more than several samples and one sample has been found to work well) so as to identify the orientation of the accelerometer (multiple samples could be averaged so as to form an estimate of orientation). The orientation of the accelerometer may be compared to the orientation of the accelerometer as determined from samples captured in one or more previous measurement periods so as to form a measure of the change in orientation over one or more measurement periods. Such a measure could be, for example, a normalised representation of the change in angle, or a measure of the variance in samples captured over a series of measurement periods. A greater measure of change in orientation indicates a higher activity level and a smaller measure of change in orientation indicates a lower activity level. The use of orientation of the motion sensor has been found to offer a good analogue for the activity level of a wearer and enables activity level to be determined on the basis of a single (or just a few) measurements performed periodically at a low frequency. The activity level may be determined at the processor 101.

Alternatively or additionally, the measure of the activity level of a wearer can be formed in dependence on the magnitude of the acceleration measured by the motion sensor in its low power mode over one or more periods. For example, a measure of activity level could be a combination (e.g. some kind of sum) of the change in angle over one or more periods with the magnitudes of the accelerations experienced by the motion sensor.

In order to ensure that the activity level is an indication of sustained rather than momentary movement by the wearer, it is preferred that the activity level is formed on the basis of acceleration data captured over multiple periods—e.g. one or more minutes. The contribution of acceleration data to a measure of activity level could be weighted such that the contribution of older samples to activity level is diminished relative to more recent samples.

In order to capture movement data for the purpose of determining vital signs, the vital signs monitor enters a second, high accuracy mode in which the motion sensor periodically measures its movement at a higher sampling rate—in the two-stage example described above this would be at an initial rate of, say, 2 Hz, which would increase on an initial estimate for the respiration rate being formed. The vital signs monitor may remain in the high accuracy mode until the required number of samples have been captured/the required length of time has elapsed so as to allow the rates of respiration and heartbeat to be determined. The vital signs monitor may then drop back into its low power mode in which it monitors the activity of the wearer at a low level. The vital signs monitor may be configured to, for example, enter its high accuracy mode according to a predefined schedule, or in response to a trigger from the processor (which may be as a result of a command or request received at the vital signs monitor from another entity, e.g. by means of transceiver 104).

It is advantageous to configure the vital signs monitor to use the activity level identified in its low power mode in a decision as to whether to enter its high accuracy mode to capture movement data for determining the rates of respiration and/or heartbeat. For example, the vital signs monitor may be configured to avoid entering its high accuracy mode when the activity level of the wearer exceeds a predefined or dynamic threshold. The activity level used could be, for example, the activity level the last time it was determined, an average activity level over a predefined period prior to the decision point, or the highest activity level within a predefined period prior to the decision point. Whilst the activity level of the wearer exceeds the threshold, the vital signs monitor may be configured to not enter its high accuracy mode to capture movement data—this may cause the vital signs monitor to abandon the scheduled or requested capture, or the monitor may defer the capture by some predetermined length of time and subsequently attempt to capture movement data to satisfy the scheduled or requested capture.

In some examples, a receiving unit 105 is present which may be a sensor adapted for measuring a physiological parameter of the wearer. For example, the receiving unit could be a temperature sensor adapted for measuring a temperature of the wearer. In examples in which the vital signs monitor is configured with a low power and high accuracy modes, temperature measurements may be performed in one or both of the low power and high accuracy modes. By providing a temperature sensor, measurements of body temperature may be captured in addition to respiration and/or heart rates, providing the monitor with data representing a further vital sign of the wearer.

Temperature measurements could be used in addition to or instead of movement data to determine when the wearer is relatively inactive and measurements of heart and/or respiration rate may be reliably performed. For instance, temperature can provide an indirect indication of the activity state of the wearer since body (typically skin) temperature tends to increase during physical activity. Also, skin temperature tends to become more variable with activity as the thermal environment of the skin changes rapidly (e.g. due to the arm moving around the armpit, or the relative movement of air over the skin as a result of motion of the wearer). Periods of relatively low and/or stable body temperatures can therefore be particularly suitable for determining vital signs through measurements of movement.

The vital signs monitor may be a temperature data logger configured to periodically or on request measure a body temperature of the wearer. Such temperature data could be acquired for the purpose (perhaps amongst others) of determining the point of ovulation in a female.

The vital signs monitor may be configured to acquire acceleration data from sensor 103 during periods of low movement activity (e.g. as determined by the accelerometer) and/or temperature. The monitor may receive an indication of movement activity at the receiving unit 105—for example, the receiving unit could be a temperature measurement indicative of activity, or the receiving unit could receive an indication from the wearer as to their activity state (e.g. as entered into their smartphone with which the monitor can communicate by means of transceiver 104).

The motion sensor 103 and processor 101 may be provided at a common integrated circuit. At least part of the processor 101 may be provided at processing functionality of an integrated circuit, chip or other package which includes the motion sensor 103.

The four primary vital signs are body temperature, blood pressure, heart (pulse) rate, and respiratory (breathing) rate. A vital signs monitor configured in accordance with any of the examples described here may measure any one or more of the four primary vital signs.

The system described above may be used for detecting that sensed data is indicative of a disease condition. That disease condition may be the onset of initial symptoms of a disease, or an exacerbation of an ongoing or chronic disease. For example, in the case of chronic obstructive pulmonary disease (COPD) during an exacerbation symptoms typically worsen for three to five days before treatment is required. By detecting worsening symptoms during that period it may be possible to intervene with therapies that avoid the need for the patient to undergo a stay in hospital.

Some non-limiting examples of diseases that could be indicated, diagnosed or monitored for using the system include chronic obstructive pulmonary disease (COPD), cystic fibrosis (CF), diabetes, hypoglycaemia, sleep disturbance, sleep apnoea, chronic pain, infection (e.g. by bacterial, viral, prion, protozoal, fungal or parasitic agents), sepsis, polycystic ovary syndrome (PCOS), menopause, asthma, insomnia, schizophrenia, coronary heart disease, narcolepsy, restless legs syndrome, rheumatoid arthritis, inflammatory bowel disease (IBD), lupus, periodic fever syndromes and cancers such as lymphoma, leukaemia and renal cancer. The sensor and the carrier may be applied to humans or animals.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A vital signs monitor for attachment to a human or animal thorax, the monitor having a low power mode and a high accuracy mode and comprising:
   a motion sensor configured to, in the low power mode, sample movement at a first frequency and, in the high accuracy mode, sample movement at a second frequency, the second frequency being greater than the first frequency; and
   a processor configured to, in the low power mode, process a series of one or more movement samples captured by the motion sensor in the low power mode so as to form a measure of activity level, and to, in the high accuracy mode, cause a series of the movement samples captured by the motion sensor in the high accuracy mode to be stored at the vital signs monitor and/or transmitted by means of a transceiver;

wherein the processor is configured to prevent the vital signs monitor entering the high accuracy mode from the low power mode when the activity level exceeds a first predefined or dynamic threshold.

2. A vital signs monitor as claimed in claim 1, wherein the processor is further configured to, in the high accuracy mode, process the series of movement samples so as to form an estimate of at least one of heart rate and breathing rate.

3. A vital signs monitor as claimed in claim 2, wherein the processor is further configured to, in the high accuracy mode, process the series of movement samples in dependence on the estimated heart rate and/or breathing rate so as to form an estimate of an amplitude of movements of the vital signs monitor due to heartbeat and/or breathing.

4. A vital signs monitor as claimed in claim 1, wherein the vital signs monitor is configured to attempt to enter high accuracy mode according to a predefined schedule or in response to a command received at a transceiver of the vital signs monitor.

5. A vital signs monitor as claimed in claim 4, wherein, in use, the vital signs monitor is coupled to a data processing system by means of the transceiver and the command is generated at the data processing system in response to an indication as to the health or perceived wellbeing of a wearer of the vital signs monitor.

6. A vital signs monitor as claimed in claim 1, further comprising a temperature sensor arranged to, in the low power mode and in use, capture a temperature of a wearer of the vital signs monitor.

7. A vital signs monitor as claimed in claim 6, wherein the vital signs monitor is configured to attempt to enter high accuracy mode and/or to increase a frequency of attempts according to the predefined schedule in response to the temperature of the wearer and/or a variance of the temperature being below a predefined or dynamic threshold in the low power mode for a first predefined or dynamically-determined period of time.

8. A vital signs monitor as claimed in claim 1, wherein the vital signs monitor is configured to attempt to enter high accuracy mode in response to the activity level of a user being below a second predefined or dynamic threshold for a second predefined or dynamically-determined period of time.

9. A vital signs monitor as claimed in claim 1, wherein the vital signs monitor is configured to attempt to enter high accuracy mode a predetermined length of time following the processor preventing the vital signs monitor from entering the high accuracy mode.

10. A vital signs monitor as claimed in claim 1, wherein the vital signs monitor is configured to revert to the low power mode once the motion sensor has stored and/or transmitted the movement samples.

11. A vital signs monitor as claimed in claim 1, wherein the processor is configured to form the measure of activity level in dependence on an orientation of the vital signs monitor as indicated by the one or more movement samples.

12. A vital signs monitor as claimed in claim 11, wherein the measure of activity level represents a change in orientation over the one or more movement samples.

13. A vital signs monitor as claimed in claim 1, wherein the motion sensor is an accelerometer.

14. A vital signs monitor as claimed in claim 1, wherein the second frequency is at least twice a highest expected breathing rate appropriate to an intended human or animal subject.

* * * * *